(12) United States Patent
Alder et al.

(10) Patent No.: US 10,595,814 B2
(45) Date of Patent: *Mar. 24, 2020

(54) COMPUTER CONTROLLED CPAP SYSTEM WITH SNORE DETECTION

(71) Applicant: ResMed Limited, Bella Vista (AU)

(72) Inventors: Matthew Alder, Scarborough (AU); Steven Paul Farrugia, Lugarno (AU); Chinmayee Somaiya, Turramurra (AU); Kristian Thomsen, Drewvale (AU)

(73) Assignee: ResMed Pty Ltd (AU)

( * ) Notice: Subject to any disclaimer, the term of this patent is extended or adjusted under 35 U.S.C. 154(b) by 409 days.

This patent is subject to a terminal disclaimer.

(21) Appl. No.: 13/710,925

(22) Filed: Dec. 11, 2012

(65) Prior Publication Data

US 2013/0178761 A1     Jul. 11, 2013

Related U.S. Application Data

(63) Continuation of application No. 12/091,809, filed as application No. PCT/AU2007/000002 on Jan. 4, 2017, now Pat. No. 8,365,729.

(Continued)

(51) Int. Cl.
*A61B 7/00* (2006.01)
*A61B 5/00* (2006.01)
(Continued)

(52) U.S. Cl.
CPC ............. *A61B 7/003* (2013.01); *A61B 5/097* (2013.01); *A61B 5/4818* (2013.01); *A61B 5/682* (2013.01);
(Continued)

(58) Field of Classification Search
CPC ....... A61B 5/097; A61B 5/4818; A61B 5/682; A61B 5/7203; A61B 5/7282; A61B 7/003;
(Continued)

(56) References Cited

U.S. PATENT DOCUMENTS 5,165,417 A   11/1992   Murphy, Jr.
5,203,343 A    4/1993   Axe et al.
(Continued)

FOREIGN PATENT DOCUMENTS

CN   1432416 A   7/2003
CN   1835775 A   9/2006
(Continued)

OTHER PUBLICATIONS

Notice of Reasons for Rejection; Japanese Application No. 2008-548907; Japanese Patent Office, dated May 31, 2011.
(Continued)

*Primary Examiner* — Kathryn E Ditmer
(74) *Attorney, Agent, or Firm* — Botos Churchill IP Law LLP

(57) ABSTRACT

A CPAP apparatus is provided that determines the presence of a snore by the simplified method of using filtered expiratory noise as the measure of intrinsic device noise and comparing that to filtered inspiratory noise. The filtering time constants for inspiratory and expiratory noise are adjusted such that treatment pressure does not cause false snore detection.

17 Claims, 2 Drawing Sheets

Related U.S. Application Data

(60) Provisional application No. 60/756,709, filed on Jan. 6, 2006.

(51) Int. Cl.
*A61M 16/06* (2006.01)
*A61B 5/097* (2006.01)
*A61M 16/00* (2006.01)

(52) U.S. Cl.
CPC ........... *A61B 5/7282* (2013.01); *A61M 16/00* (2013.01); *A61M 16/0066* (2013.01); *A61M 16/0069* (2014.02); *A61M 16/0666* (2013.01); *A61M 2205/3375* (2013.01)

(58) Field of Classification Search
CPC .............. A61M 16/00; A61M 16/0069; A61M 16/0066; A61M 16/0666; A61M 2205/3375
USPC ................ 128/204.23, 204.26; 600/529, 538
See application file for complete search history.

(56) References Cited

U.S. PATENT DOCUMENTS

| | | | |
|---|---|---|---|
| 5,245,995 | A | 9/1993 | Sullivan et al. |
| 5,551,419 | A | 9/1996 | Froehlich et al. |
| 5,704,345 | A | 1/1998 | Berthon-Jones |
| 5,989,193 | A | 11/1999 | Sullivan |
| 6,705,315 | B2 | 3/2004 | Sullivan et al. |
| 6,790,183 | B2 | 9/2004 | Murphy |
| 6,840,907 | B1 | 1/2005 | Brydon |
| 7,850,619 | B2 * | 12/2010 | Gavish et al. ................ 600/538 |
| 2002/0007127 | A1 | 1/2002 | Sullivan et al. |
| 2003/0066529 | A1 | 4/2003 | Truschel et al. |
| 2005/0065560 | A1 | 3/2005 | Lee et al. |

FOREIGN PATENT DOCUMENTS

| | | |
|---|---|---|
| JP | H02-13453 | 1/1990 |
| WO | 1986005965 A1 | 10/1986 |
| WO | 8700415 A1 | 1/1987 |
| WO | 1987000415 A1 | 1/1987 |
| WO | 1988010108 | 12/1988 |
| WO | 92-22244 A1 | 12/1992 |
| WO | 2003030716 A2 | 4/2003 |
| WO | 2004066804 A2 | 8/2004 |
| WO | WO 2004066804 A2 * | 8/2004 |
| WO | 2005074361 A2 | 8/2005 |
| WO | WO 2005120167 A2 * | 12/2005 |

OTHER PUBLICATIONS

Sullivan CE, et al. Reversal of obstructive sleep apnea by continuous positive airway pressure applied through the Lancet Apr. 18, 1981:1(8225):862-5.

Australian Examination Report for Application No. 2007203731 dated Jun. 29, 2012.

Extended European Search Report for Application No. EP13161245 dated Jul. 30, 2013.

* cited by examiner

COMPUTER CONTROLLED CPAP SYSTEM WITH SNORE DETECTION

CROSS-REFERENCE TO RELATED APPLICATIONS

The present application is a continuation of U.S. patent application Ser. No. 12/091,809, filed on Jun. 30, 2008, which application is a national phase entry under 35 U.S.C. § 371 of International Application No. PCT/AU2007/000002 filed Jan. 4, 2007, which claims the benefit of the filing date of U.S. Provisional Patent Application No. 60/756,709 filed Jan. 6, 2006, all of which are hereby incorporated herein by reference.

FIELD OF INVENTION

This invention relates to methods and apparatus for the provision of positive pressure ventilatory assistance for patients with sleep disordered breathing. In particular it relates to the recognition of snoring during therapy.

BACKGROUND OF THE INVENTION

Sleep-disordered breathing (SDB) encompasses a group of disorders where the breathing pattern or quality of ventilation is abnormal during sleep. Obstructive sleep apnea (OSA), the most common such disorder (affecting a possible 4-50 of the adult population), is characterized by repetitive closing or collapse of the upper airway and partial or complete diminution of breathing. The obstruction is normally ended by the patient arousing briefly when the muscles of the upper airway act to clear the obstruction. The treatment of choice for OSA is continuous positive airway pressure (CPAP) as first described by Sullivan [Sullivan C E, et al. Reversal of obstructive sleep apnea by continuous positive airway pressure applied through the nares. Lancet 1981 Apr. 18; 1(8225):862-5].

CPAP devices are particularized for the patient through a process known as titration in which the minimum pressure necessary to keep the airway open is determined. Excessive pressure leads to patient discomfort and interrupted sleep. The minimum required pressure may vary during the patient's sleep cycle, and accordingly auto-titrating devices have been developed that monitor the patient's respiration to determine and adjust the pressure as appropriate. In addition, some devices provide dual pressure levels in an attempt to make the patient more comfortable, providing greater positive pressure during inspiration than during expiration. Such devices monitor the patient's respiration cycle in order to switch between pressure levels at the appropriate phase in the respiration of each breath. Depending on their conditions, different patients may experience different levels of discomfort depending upon how quickly and accurately the device tracks the patients' efforts. Simple threshold tests may fail when breaths are irregular, for example, during the presence of coughs, sighs and snores.

OSA is often accompanied by snoring. Thus many CPAP devices seek to determine the occurrence of snoring and to quantify it. For example, U.S. Pat. No. 6,840,907, issued Jan. 11, 2005 provides a device having a sensor array and processor, which is capable of analyzing snore. In particular it measures the snore amplitude of the patient by passing digitized snoring signals through a high pass filter with a low frequency cut-off of approximately 10 Hz, calculating the modulus of each resulting signal, summing all the moduli and passing the sum through a low pass filter with a high frequency cut-off of between 0.5 and 2 Hz. The processor also measures the harmonic purity of the patient's snore, that is, its closeness in form to a simple sine wave—on the assumption that a non-obstructive snore has a different degree of harmonic purity than an obstructive one. Further the system produces a measure of the harmonic stability of the patient's snore, that is, the accuracy with which one cycle of the snore signal matches its predecessor—on the assumption that a non-obstructive snore has a different degree of harmonic stability than an obstructive one.

U.S. Pat. No. 6,705,315 describes a CPAP apparatus having a sound transducer and a system that responds to sound indicative of snoring.

For effective delivery of treatment pressure in an auto-titrating CPAP device, the treatment should be applied at the first sign of impending obstruction. In many patients, an apneic (obstructive) episode is often preceded by a snore. Therefore, detection of snore is crucial to pre-emptive delivery of therapy.

Current snore detection/estimation technique requires extensive modeling of various patient air paths and resulting complex calibration. According to the prior art, snore is the residual noise in region 20-300 hz after removing an estimation of motor and other extraneous noise from the total noise estimate. To estimate motor noise, a model of noise is obtained empirically for every possible combination of air path elements. This is then utilized to arrive at patient snore during delivery of pressure therapy. Essentially Snore=Total Noise-Intrinsic Device Noise. The complex methods for calculating intrinsic device noise adds considerable cost to the production of flow generator and also to each incremental design change in air path of the flow generator.

What is needed is an economical, simplified method for detecting snoring in a patient receiving pressurized air from a CPAP device.

BRIEF DESCRIPTION OF THE INVENTION

A simplified method for identifying a snore in a CPAP device is achieved by detecting the noise level from an appropriate sensor in the device and taking advantage of the fact that the noise from snoring occurs only during the inspiration portion of the breathing cycle. A significant difference, i.e. above a predetermined threshold, between noise levels during inspiration and expiration is used to indicate snoring. This avoids the necessity to account for or model all sources of noise during the operation of the CPAP device. The present invention involves using a sensor, for example a microphone, to detect snore. However other sensors such as pressure or flow sensors may also be used.

The preferred embodiment of the invention involves 1) using expiratory noise as the measure of intrinsic device noise, hence eliminating any need to calibrate device noise as a function of patient circuit parameters; 2) Using inspiratory noise as the carrier of patient snore; 3) adjusting the filtering time constant for inspiratory and expiratory noise such that treatment pressure does not cause false snore detection.

DETAILED DESCRIPTION OF A PREFERRED EMBODIMENT OF THE INVENTION

Figure 1A:
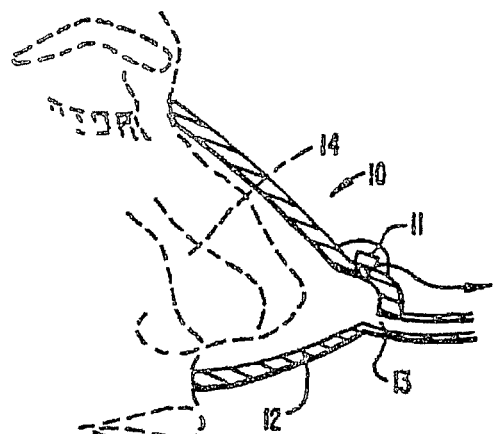
FIG. 1a is a schematic sectional view of one embodiment of a snoring detection apparatus in accordance with the present invention.
Figure 1B:
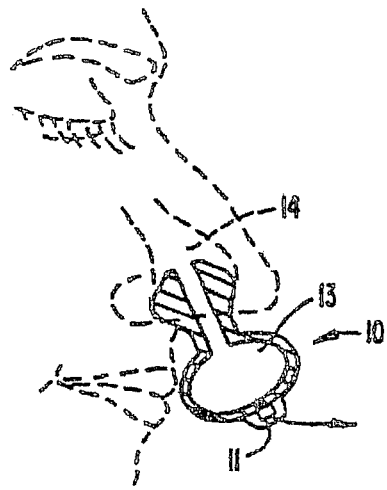
FIG. 1b is a schematic sectional view of another embodiment of a snoring detection apparatus in accordance with the present invention.

FIG. 1a illustrates a snoring detection device 10 comprising a microphone 11, in sound communication with the container 12 of a nose mask. Air, being inhaled by the patient, enters the nasal passageways 14 through the opening in the nose mask 12 and is exhaled in the reverse direction. As the airway extends from the source of snoring sounds within the patient's body, through the nasal passages 14 and out of the opening 13 in the nasal mask, the microphone is ideally located to take advantage of the natural stethoscope formed by the enclosed airway. Hence the snoring and breathing sounds are focused and concentrated by this arrangement. Alternatively, the microphone 11 may be located within, or attached externally of, a nasal prong device as illustrated in FIG. 1b.

Figure 2:
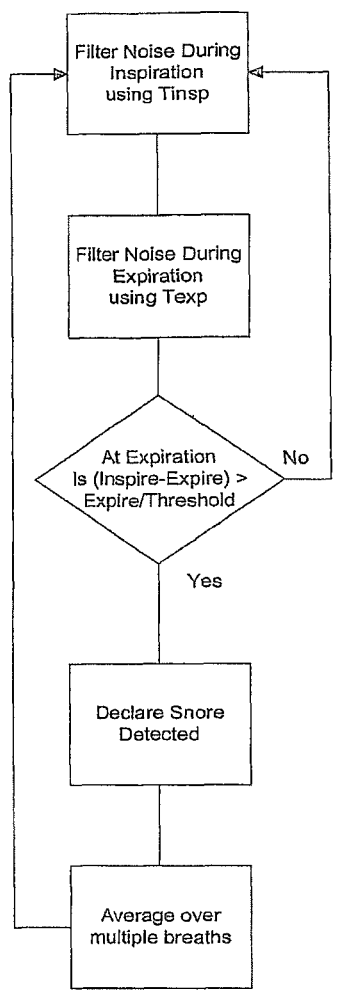
FIG. 2 is a flow chart of the steps of present invention.

As depicted in FIG. 2, snoring is detected according to the following steps:

During inspiration, InspiratorySnore is measured as the noise filtered during inspiration with a time constant Tinsp During expiration, ExpiratorySnore is measured as noise filtered during expiration with a time constant Texp.

Tinsp>Texp in order to ensure that treatment pressure change does not cause false detection of snore.

At the time of entry to expiration, if (InspiratorySnore−ExpiratorySnore)>ExpiratorySnore/ThresholdFactor, snore is said to have been detected.

This value is then filtered over a plurality of breaths (e.g. 5 breaths) to derive an average snore value.

Figure 3:
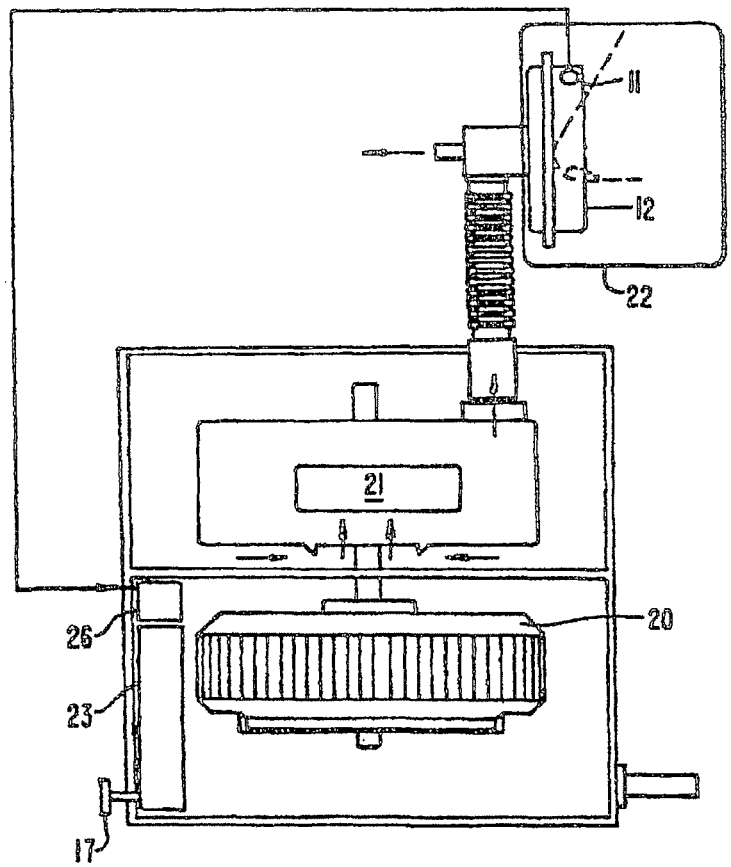
FIG. 3 is a diagram of a further embodiment of the present invention.

In FIG. 3, a CPAP apparatus embodying the invention is illustrated. The CPAP unit comprises a motor 20 which drives a blower 21. The speed of the motor 20 is controlled by an electronic speed control unit 23. As an increase in motor speed also increases the blower speed which in turn increases the output air pressure of the blower 21, the speed control unit can be manipulated to vary the output pressure of the blower 21. The CPAP device also includes a snoring detection means 22 wherein sounds are detected by a microphone 11. In its most general form, the snoring detection means 22 is a pressure detection means and microphone 11 is a differential pressure sensor. The snoring detection means 22 is conveniently in the form of the previously described device 10. Electrical impulses are fed from said microphone 11 to an amplifier/filter/processor unit 26 which generates an electrical signal when snoring sounds occur. The motor speed control means is electrically connected to the snoring detection device 22 and increases the speed of the electric motor 20 by an analogue means in response to the electrical signal generated by the snoring detection device. Accordingly, the output pressure of the CPAP unit increases in response to detection of snoring.

When a snore or sequence of snores is detected by the snoring detection means 22, a signal is generated. The speed control unit 23 increases the speed of the fan motor and the output pressure is increased. As snoring is caused by vibration of the soft palate, it is therefore indicative of an unstable airway and, as previously described, is a warning signal of the imminence of upper airway occlusion, in patients that suffer obstructive sleep apnea. Snoring is itself undesirable, not only as it is a disturbance to others, but it is strongly believed to be connected with hypertension. If the resultant increase in CPAP pressure is sufficient to completely stabilize the airway, snoring will cease. If a further snoring sound is detected, the CPAP pressure is increased again. This process is repeated until the upper airway is stabilized and snoring ceases. Hence, the occurrence of obstructive apnea can be eliminated by application of minimum appropriate pressure at the time of use.

In order to ensure that the CPAP pressure is maintained at a level as low as practicable to prevent the onset of apnea, the preferred embodiment also includes a means to decrease the pressure if an extended period of snore free breathing occurs. For example, this can be done by automatically reducing the CPAP pressure at a gradual rate as long as snoring is not detected. The rate at which the CPAP pressure is decreased in the absence of snoring is preferably much less than the rate at which it is increased when snoring is detected. This can be achieved, for example, by the amplifier/filter/processor unit 26, in the absence of snore detected from the microphone 11, continuously gradually reducing the blower speed over a period of time but increasing the blower speed in incremental steps each time a snore is detected by the microphone 11

At the time of entry to expiration, if (Inspiratory Snore−Expiratory Snore)>Expiratory Snore/ThresholdFactor, snore is said to have been detected.

The method of operation can be illustrated by considering the effect of a snore or sequence of snores detected by the pressure sensor as shown in FIG. 13. When a snore or sequence of snores is detected by the snoring detection means 22 a signal is generated. The speed control unit 23 increases the speed of the fan motor and the output pressure is increased. As snoring is caused by vibration of the soft palate, it is therefore indicative of an unstable airway and, as previously described, is a warning signal of the imminence of upper airway occlusion in patients that suffer obstructive sleep apnea. Snoring is itself undesirable not only as it is a disturbance to others but it is strongly believed to be connected with hypertension. If the resultant increase in CPAP pressure is sufficient to completely stabilize the airway, snoring will cease. If a further snoring sound is detected, the CPAP pressure is increased again. This process is repeated until the upper airway is stabilized and snoring ceases. Hence, the occurrence of obstructive apnea can be eliminated by application of a minimum appropriate pressure at the time of use.

In use a patient may connect himself to the CPAP unit and go to sleep. A single connection to the patient is required from the normal CPAP circuit together with a further connection from the pressure sensor to the amplifier/filter/processor unit. No electrodes or other sensors have to be attached to the patient's body as the pressure sensor may be conveniently located in the CPAP mask. Alternatively, the sensor need not be at the mask but in the flow generator. The CPAP pressure is initially at a minimum comfortable operating value of, for example, approximately 3 cm H.sub.20 gauge pressure so the as not to cause the previously mentioned operational problems of higher initial pressures. Not until some time after going to sleep, and the patient's body relaxes, will the airway start to become unstable and the patient start to snore or exhibit abnormal breathing patterns. The detection apparatus 22 will a respond to the snore, or snore pattern or an abnormal breathing pattern and via the processor 26 increase the motor speed such that CPAP pressure increases by 1 cm H.sub.20 for each snore or predetermined abnormality in breathing pattern detected. The CPAP pressure can be increased relatively rapidly, if the patient's condition so requires, to a working pressure of the order of 8-10 cm H.sub.20, which is a typical requirement.

An upper pressure limiting device can be incorporated for safety. Also, for ease of monitoring the variation over time in patient conditions, a parameter such as pressure output can be recorded in some convenient retrievable form for periodic study by the physician.

By continuously decreasing the CPAP pressure as a rule of, for example, 1 cm H.sub.20 each 15 mins or by ⅓ in 20 minutes, in the absence of snoring or abnormal breathing patterns, the pressure is never substantially greater than that required to prevent apnea or other undesirable respiratory conditions. However, when a snore, or snoring patterns or abnormal breathing pattern, is detected the decreasing CPAP pressure mode will be completely overwhelmed by a greater increase, about 1 cm H.sub.20 per predetected snore or snoring pattern or predetermined abnormality in breathing pattern, subject to a slew rate that prevents instantaneous pressure increases, and limits pressure increases to 1 cm/s. Once a stable sleeping pattern is achieved, the preferred embodiment will continually test to ensure that the CPAP pressure is as low as is practicable. Should the CPAP pressure be decreased to such an extent that the upper airway becomes unstable and snoring or unacceptable breathing patterns recommence, the pressure is reincreased to ensure that apnea or snore or abnormal breathing are prevented, it being remembered that the snoring or abnormal breathing pattern is a precursor to apneic episodes or other undesirable respiratory conditions such as shallow breathing or hypopnea.

It is known that a patient's maximum propensity to suffer sleep apnea occurs during REM sleep. An airway that was otherwise stable at a given CPAP pressure may become unstable during REM sleep. Should this happen snoring and/or particular deviations in breathing patterns will set in before apnea occurs. In such circumstances, the present invention will raise the CPAP pressure in response to the snoring or deviation in breathing patterns, thus preventing the onset of apnea or other undesirable respiratory condition. After the REM sleep passes, the patient's airway becomes more stable and the higher airway pressure is no longer required. In such circumstances, the CPAP pressure will be gradually reduced until the first sign of snoring and/or unacceptable breathing patterns reoccurs at which point the pressure will again be increased.

A patient normally makes at least one loud snort or snoring sound at the end of an occurrence of apnea and the present invention will respond to this unusually loud sound to increase the CPAP pressure. Thus even if apnea should occur without the usual precursor of snoring or abnormal breathing pattern, the airway pressure can still be adjusted upward in response to the abnormally loud breathing sounds generated at the end of the apneic period.

The present invention thus provides a CPAP device which modifies the CPAP pressure according to variations in a patient's requirements throughout an entire sleep period. It will be clear to those skilled in the art that the present invention can cope with the variation in airway pressure requirements such as may occur during a single sleep period, it will also be able to cope with variations in CPAP pressure requirements due to a general improvement or deterioration in a patient's general condition as may take place over a longer period of time.

It is to be understood that while the invention has been described above in conjunction with preferred specific embodiments, the description and examples are intended to illustrate and not limit the scope of the invention, which is defined by the scope of the appended claims.

The invention claimed is:

1. A continuous positive airway pressure (CPAP) device for treating sleep disordered breathing, the CPAP device comprising:
   a blower to generate a supply of pressurized air; and
   a snoring detection device, comprising:
      a sensor configured to detect sounds during a breathing cycle; and
      a processor configured to:
         detect a noise level during an inspiration phase of the breathing cycle with the sensor;
         detect a noise level during an expiration phase of the breathing cycle with the sensor; and
         determine an occurrence of a snore based on a difference in the noise levels detected during inspiration and expiration, the difference comprising a subtraction of the noise level during expiration from the noise level during inspiration,
   wherein the CPAP device further comprises a motor configured to drive the blower and a motor speed controller, and
   wherein the snoring detection device is connected to the motor speed controller to allow adjustment of the motor speed in response to a signal indicative of a snore value from the determination of the occurrence of a snore.

2. The CPAP device according to claim 1, wherein the processor is configured to determine an inspiratory snore value, used to determine the snore value, is determined from a filtered noise level detected during the inspiration phase and an expiratory snore value, used to determine the snore value, from a filtered noise level detected during the expiration phase, wherein the sensor is in sound communication with a mask.

3. The CPAP device according to claim 2, wherein the processor is configured to determine the occurrence of the snore based on the inspiratory snore value, the expiratory snore value and a threshold.

4. The CPAP device according to claim 1, wherein the processor is configured to determine the occurrence of a snore based on a comparison between the difference in the noise levels and a threshold.

5. The CPAP device according to claim 4, wherein the processor further filter the signal indicative of the snore value over multiple breaths and report the filtered signal as an average snore value.

6. The CPAP device according to claim 1, wherein the processor is configured to use the noise level during the inspiration phase to determine an inspiratory snore value during inspiration by filtering, and
   the noise level during the expiration phase to determine an expiratory snore value during expiration by filtering.

7. The CPAP device according to claim 6, wherein a time constant for filtering in the determination of the inspiratory snore value during inspiration is greater than a time constant for filtering in the determination of the expiratory snore value during expiration.

8. The CPAP device according to claim 6, wherein the processor is configured to determine the occurrence of the snore if a difference between filtered noise levels exceeds a ratio of the expiratory snore value to a predetermined threshold.

9. The CPAP device according to claim 1, wherein the sensor is a pressure sensor.

10. The CPAP device according to claim 1, wherein the sensor is a microphone.

11. The CPAP device according to claim 1, wherein the processor is configured to:

detect the noise level during the inspiration phase with the sensor and determine from the noise level an inspiratory snore value during the inspiration phase by filtering, detect the noise level during the expiration phase with the sensor and determine from the noise level an expiratory snore value during the expiration phase by filtering, and determine the occurrence of the snore if a difference between the inspiratory snore value and the expiratory snore value exceeds a ratio of the expiratory snore value to a predetermined threshold, and wherein the sensor is in sound communication with a nasal prong device.

12. The CPAP device according to claim 11, wherein the processor is further configured to filter the signal indicative of the snore value over multiple breaths and to report the filtered value as an average snore value.

13. The CPAP device according to claim 11, wherein the sensor is a pressure sensor.

14. The CPAP device according to claim 11, wherein the sensor is a microphone.

15. The CPAP device according to claim 11, wherein a time constant for filtering in the determination of the inspiratory snore value during the inspiration phase is greater than (>) a time constant for filtering in the determination of an expiratory snore value during the expiration phase.

16. The CPAP device according to claim 15, wherein the sensor is a pressure sensor.

17. The CPAP device according to claim 15, wherein the sensor is a microphone.

* * * * *